US008610585B1

(12) United States Patent
Kielbasa et al.

(10) Patent No.: US 8,610,585 B1
(45) Date of Patent: Dec. 17, 2013

(54) ELECTRONIC ALERTING DEVICE AND ASSOCIATED METHOD

(76) Inventors: Matthew Kielbasa, San Diego, CA (US); Michael Kielbasa, San Diego, CA (US)

(*) Notice: Subject to any disclaimer, the term of this patent is extended or adjusted under 35 U.S.C. 154(b) by 240 days.

(21) Appl. No.: 12/880,587

(22) Filed: Sep. 13, 2010

Related U.S. Application Data

(60) Provisional application No. 61/267,249, filed on Dec. 7, 2009.

(51) Int. Cl.
*G08B 21/06* (2006.01)
(52) U.S. Cl.
USPC ........ 340/575; 340/576; 340/693.9; 382/181; 180/271; 180/272
(58) Field of Classification Search
USPC ........ 340/575, 576, 693.9; 382/181; 180/271, 180/272
See application file for complete search history.

(56) References Cited

U.S. PATENT DOCUMENTS

| | | | |
|---|---|---|---|
| 4,875,030 A | 10/1989 | Chiu | |
| 6,067,020 A * | 5/2000 | Wimmer | 340/575 |
| 6,154,141 A | 11/2000 | Prater et al. | |
| 7,126,485 B2 | 10/2006 | Cece et al. | |
| 7,301,465 B2 * | 11/2007 | Tengshe et al. | 340/575 |
| 2004/0090334 A1 * | 5/2004 | Zhang et al. | 340/575 |

OTHER PUBLICATIONS

Oakley, Inc., Razrwire "Quick Start Guide", Motorola, Sep. 28, 2006, 12 pages.
Time NewsFeed, "New Auto Technology Can Tell When You're 'Driving While Drowsy'", retrieved from http://newsfeed.time.com/2011/1/106/new-auto-technologv-can-tell-when-youre-driving-while-drowsy/ , on Oct. 6, 2011, 7 pages.

* cited by examiner

*Primary Examiner* — Daniel Wu
*Assistant Examiner* — Benyam Haile
(74) *Attorney, Agent, or Firm* — Joseph J. Mayo; ARC IP Law, PC

(57) ABSTRACT

An electronic alerting device may include an earpiece adapted to be worn at the driver ear. The earpiece may include a microchip and a sensor located at an outer surface of the earpiece. The sensor may be capable of detecting when the driver eyelid closes and opens by generating and transmitting eyelid detection signals to the microchip when the driver eyelid closes and opens respectively. A transducer may be attached to the earpiece and adapted to be placed in the driver ear. A communication interface may be used to enable the microchip to communicate with the transducer. The microchip may determine a number of continuous occurrences of the eyelid detection signals and thereby generates and transmits control signals to the transducer when the number of continuous occurrences of the eyelid detection signals is above and below a threshold number of continuous occurrences within a unit of time.

11 Claims, 6 Drawing Sheets

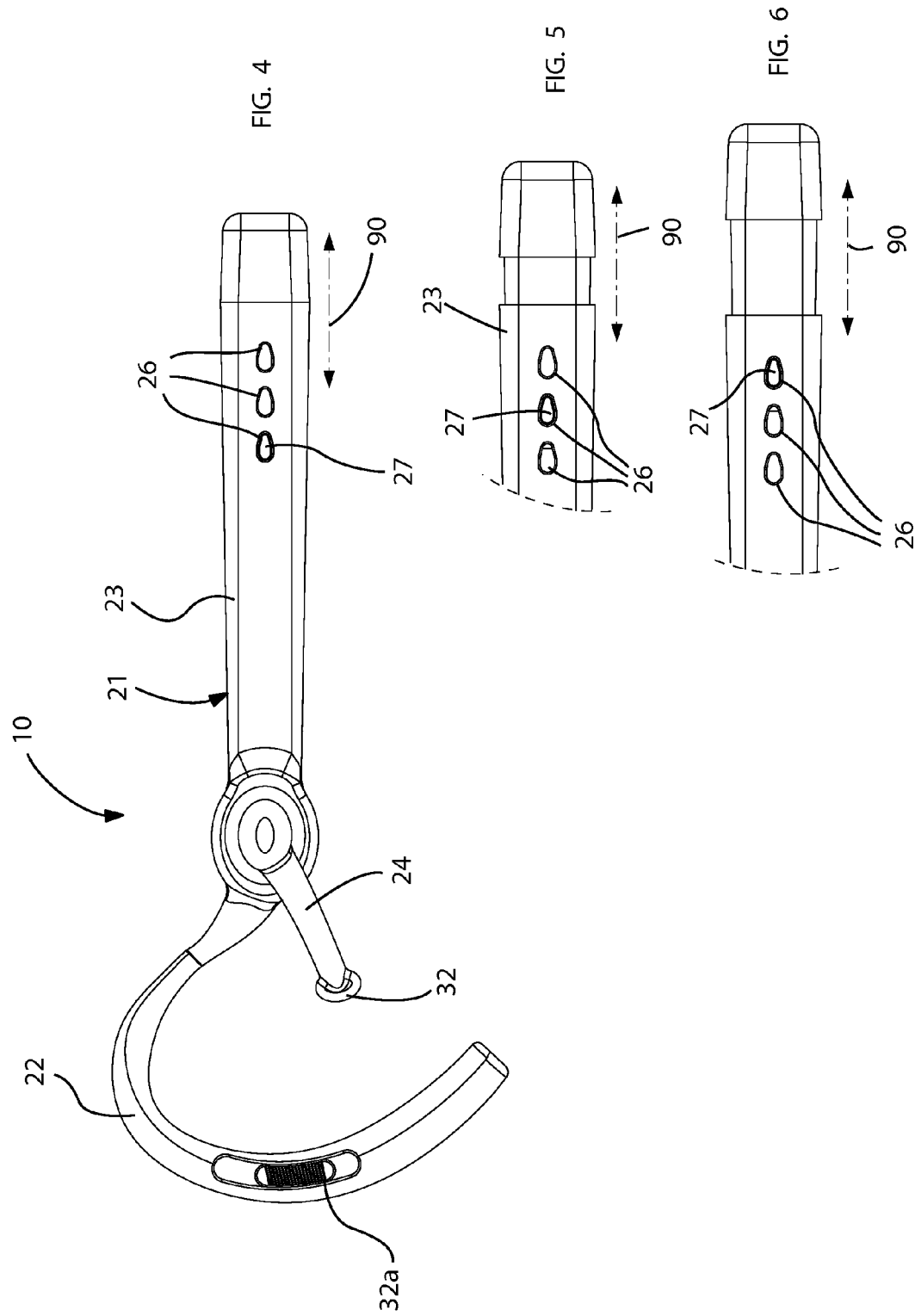

ELECTRONIC ALERTING DEVICE AND ASSOCIATED METHOD

CROSS REFERENCE TO RELATED APPLICATIONS

This application claims the benefit of U.S. Provisional Application No. 61/267,249, filed Dec. 7, 2009, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to alarm systems and, more particularly, to an electronic alerting device for providing users with an easy and convenient means of rousing them should they fall asleep while driving a vehicle.

2. Prior Art

The dangers of drinking alcohol before driving are widely known. But far too many people think little of slumping behind the wheel while fatigued, or continuing to drive while feeling drowsy. A recent survey of more than 1,000 Americans by the National Sleep Foundation found 57 percent had driven while drowsy in the past year and 23 percent had fallen asleep at the wheel. Experts estimate weary motorists who drift off the road and crash cause about 40,000 injuries and 1,550 deaths nationally each year. Symptoms of fatigue include involuntary eye closures, yawning, feeling tired, inability to stay in a lane and inattention. Fatigue can occur at any time of day, and safety experts say drivers who feel drowsy should take the feeling seriously. Sleep can strike without warning; it only takes a second to shut your eyes, leave your lane and crash. As such, it is typical for drowsy drivers not to realize they are falling asleep. Many drivers believe they can stay awake by rolling down the window or turning up the radio, but safety experts say these techniques simply do not work.

Accordingly, a need remains for an alarm system in order to overcome the above-noted shortcomings. The present invention satisfies such a need by providing an electronic alerting system that is convenient and easy to use, is durable yet lightweight in design, is versatile in its applications, and provides users with an easy and convenient means of rousing them should they fall asleep while driving a vehicle.

BRIEF SUMMARY OF THE INVENTION

In view of the foregoing background, it is therefore an object of the present invention to provide an apparatus to be worn on an ear of a driver for ensuring that the driver remains alert while operating a vehicle. These and other objects, features, and advantages of the invention are provided by an electronic alerting device.

The electronic alerting device may include an earpiece adapted to be worn at the driver ear. The earpiece may include a microchip housed therein and a sensor may further be located at an outer surface of the earpiece. The sensor may be capable of detecting when the driver eyelid closes and opens by generating and transmitting first and second eyelid detection signals to the microchip when the driver eyelid closes and opens respectively. A transducer may be attached to the earpiece and adapted to be placed in the driver ear. A communication interface may be used to enable the microchip to communicate with the transducer.

In this way, the microchip may determine a number of continuous occurrences of the first and second eyelid detection signals per a unit of time and thereby generates and transmits true and false control signals to the transducer when the number of continuous occurrences of the first and second eyelid detection signals is above and below a threshold number of continuous occurrences within the unit of time respectively. Such an arrangement provides the unexpected and unpredictable advantage of wearing the device on the driver's ear so that the sensor may be in close proximity to the eyelid in order to detect the opening and closing of the driver's eye, and thus determine the first and second eyelid detection signals without been affected by movements of the other parts of the driver's face or nearby objects.

The microchip may include a processor and a memory communicatively coupled to the processor. The memory may include software instructions, and when executed by the processor may cause the transducer to selectively emit an alert signal. The software instructions may include a control logic algorithm. Such a control logic algorithm may include the chronological steps of: upon receiving an initial signal of the first and second eyelid detection signals, determining whether the initial signal is the first eyelid detection signal; if yes, initiating a time count; if no, repeating step a.; upon receiving a subsequent signal of the first and second eyelid detection signals, determining whether the initial signal is unique to the subsequent signal; if the initial signal is unique to the subsequent signal, ending the time count and repeating step a.; if the initial signal is the same as the subsequent signal, ending the time count and counting the number of continuous occurrences of the first eyelid detection signals; if the number of continuous occurrences of the first eyelid detection signal is above the threshold number of continuous occurrences within the unit of time, generating and transmitting the true control signal to the transducer; and if the number of continuous occurrences of the first eyelid detection signal is below the threshold number of continuous occurrences within the unit of time, generating and transmitting the false control signal to the transducer. Such a control algorithm provides the unexpected and unpredictable advantage of detecting the driver's eye when it is closed for an abnormal length of length and to activate the transducer to emit an audio alarm into the driver's ear before the driver falls asleep at the wheel.

The earpiece may include a hook-shaped member having an arcuate-shaped proximal end portion and a linear distal end portion. The arcuate-shaped proximal end portion may be adapted to be positioned about the driver ear. The linear distal end portion may be adapted to terminate at a corner of the driver eyelid. A flange member may be outwardly extended from the hook-shaped member and adapted to be inserted into the driver ear. The transducer may further be attached to a tip of the flange member. Such an arrangement provides the unexpected and unpredictable advantage of ergonomically positioning the ear piece in such a manner that the user may wear the device with ease and comfort. One skilled in the art may understand that such a device must be comfortably worn by the user in order to be effective at all times when in use.

The linear distal end portion may further be linearly reciprocated along an axial path while the proximal end portion remains positioned about the driver ear. Such an arrangement provides the unexpected and unpredictable advantage of adjusting the sensor to an optimum distance from the driver eyelid thereby eliminating any errors in sensing the eyelid movements.

The invention may include a method of utilizing an electronic alerting device adapted to be worn on an ear of a driver for ensuring that the driver remains alert while operating a vehicle. Such a method may include the chronological steps of: providing an earpiece including a microchip housed therein; providing and locating a sensor at an outer surface of the earpiece; providing and attaching a transducer to the earpiece; providing a communication interface for enabling the microchip to communicate with the transducer; wearing the earpiece at the driver ear; placing the transducer in the driver ear; upon detecting when a driver eyelid closes and opens, the sensor generating and transmitting first and second eyelid detection signals to the microchip respectively; the microchip determining a number of continuous occurrences of the first and second eyelid detection signals per a unit of time; and the microchip generating and transmitting true and false control signals to the transducer when the number of continuous occurrences of the first and second eyelid detection signals is above and below a threshold number of continuous occurrences within the unit of time respectively.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

FIG. 4 is a front elevational view of the apparatus showing the location of the indent in a first hole position;

FIG. 5 shows the location of the indent in a second hole position;

FIG. 6 shows the location of the indent in a third hole position;

Figure 1:
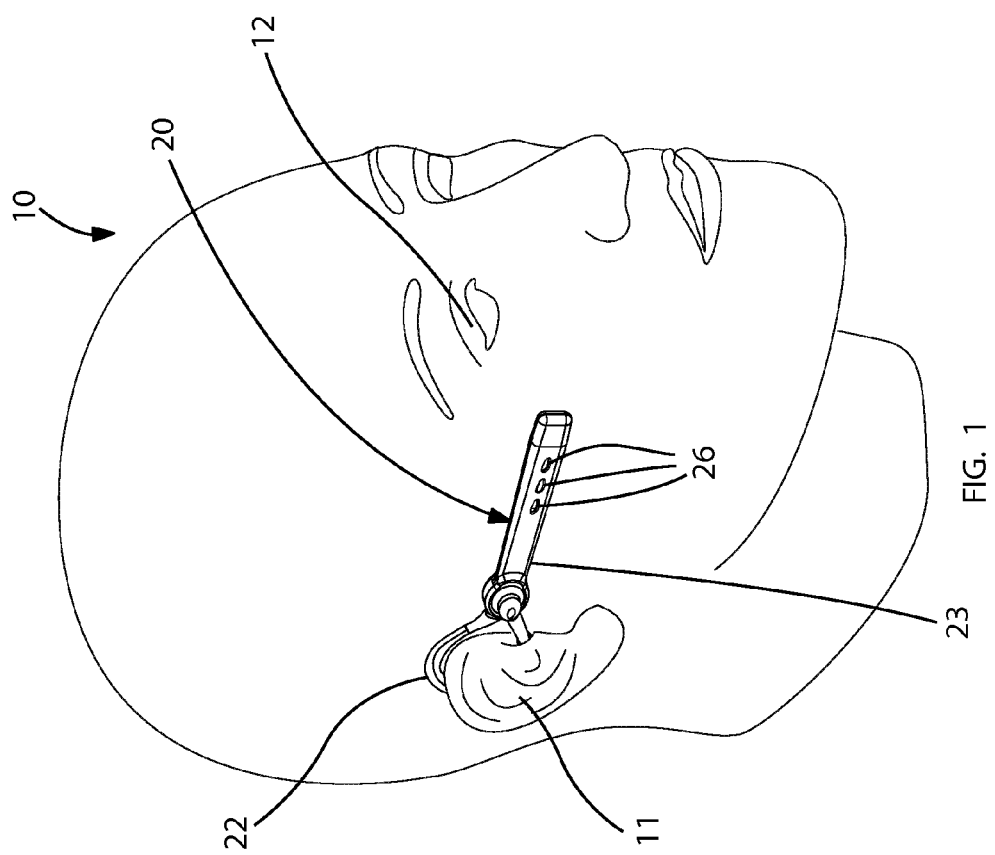
FIG. 1 is a perspective view showing an electronic alerting device worn on the ear of a vehicle driver, in accordance with the present invention.
Figure 2:
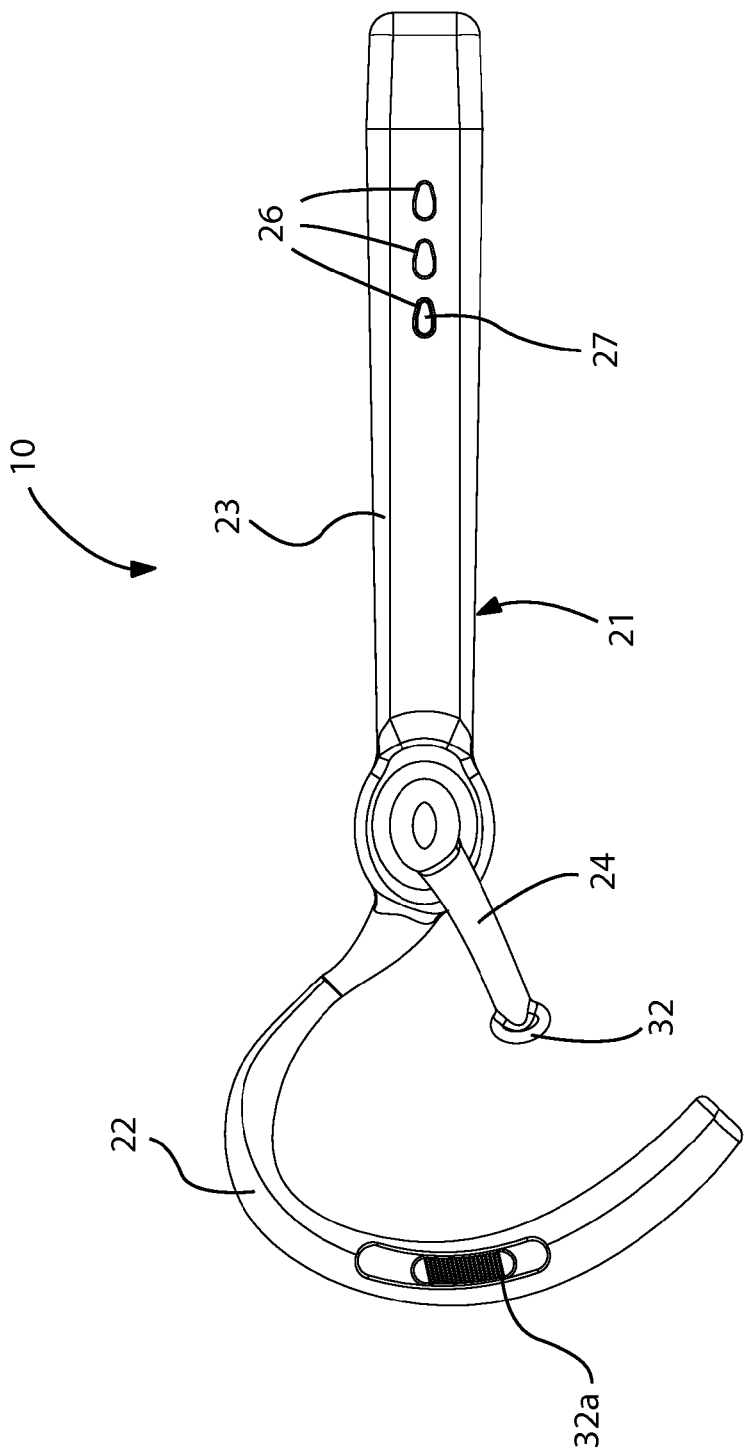
FIG. 2 is a front elevational view of the apparatus showing the location of the transducer.
Figure 3:
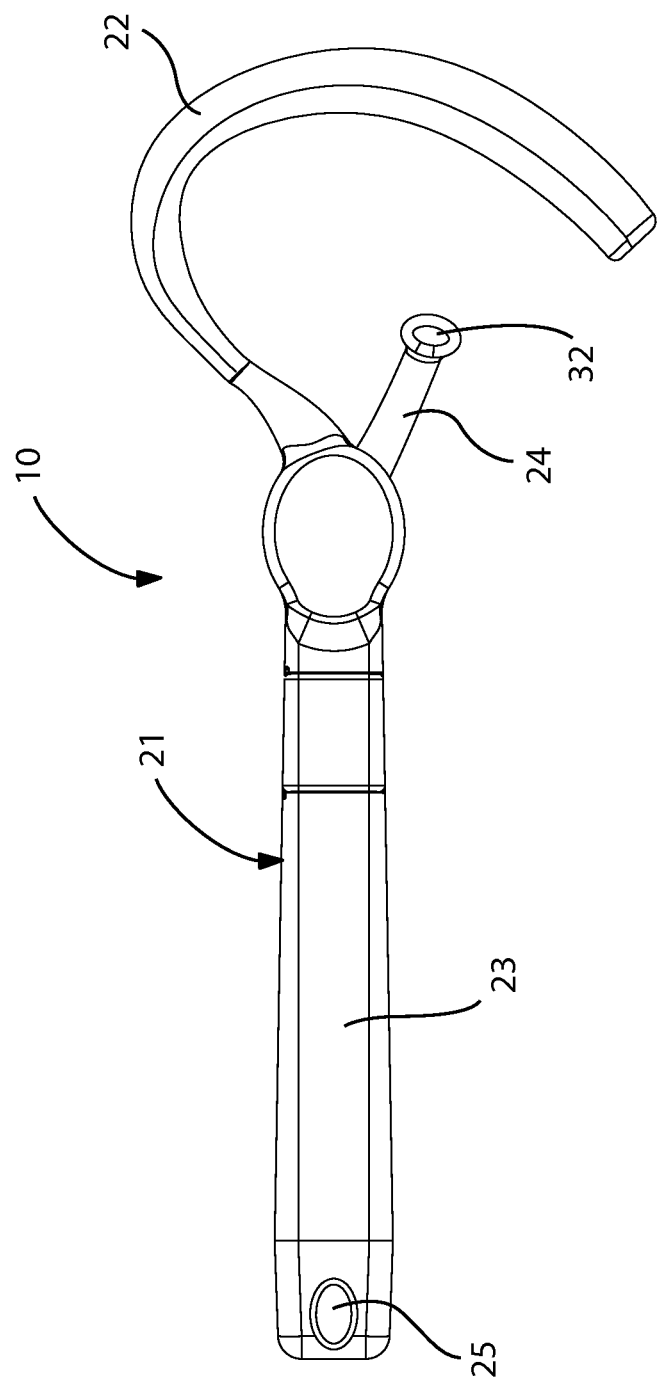
FIG. 3 is a rear elevational view of the apparatus shown in FIG. 2.
Figure 7:
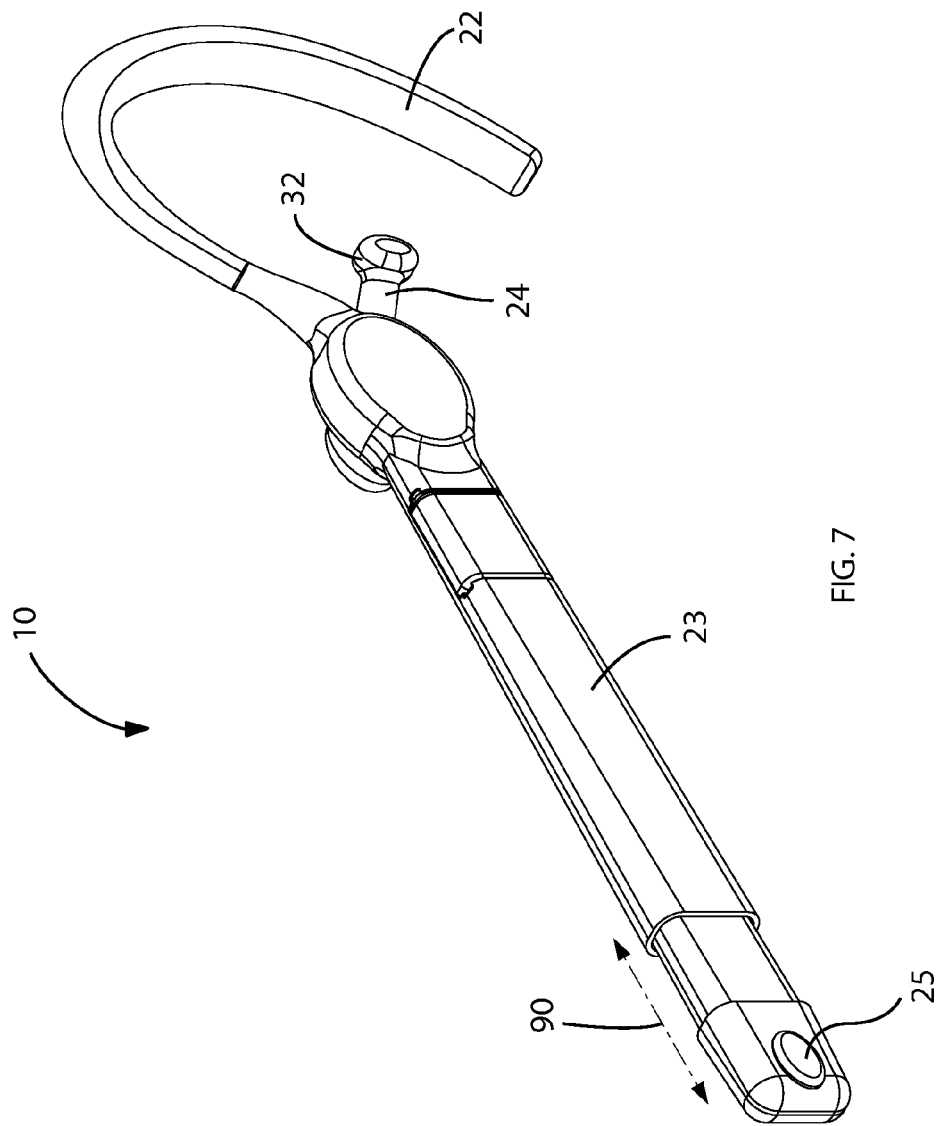
FIG. 7 is a rear elevation view of the device showing the location of the sensor.

Those skilled in the art will appreciate that the figures are not intended to be drawn to any particular scale; nor are the figures intended to illustrate every embodiment of the invention. The invention is not limited to the exemplary embodiments depicted in the figures or the shapes, relative sizes or proportions shown in the figures.

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "present invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. §1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The below disclosed subject matter is to be considered illustrative, and not restrictive, and the appended claims are intended to cover all such modifications, enhancements, and other embodiments which fall within the true scope of the present invention. Thus, to the maximum extent allowed by law, the scope of the present invention is to be determined by the broadest permissible interpretation of the following claims and their equivalents, and shall not be restricted or limited by the foregoing detailed description.

The apparatus of this invention is referred to generally in FIGS. 1-8 and is intended to provide an electronic alerting device. It should be understood that the present invention may be used to rouse users should they fall asleep while driving a vehicle or in many other different types of work situations, and should not be limited to the uses described herein.

Referring generally to FIGS. 1-8, the electronic alerting device 10 may include an ear piece 20 adapted to be worn at the driver ear 11. The ear piece 20 may include a microchip 31 housed therein and a sensor 25 may further be located at an outer surface of the ear piece 20. Notably, earpiece 20 is suitably sized and shaped so that sensor 25 lays proximate to a corner of the driver's eyelid and thereby capable of detecting movement of the eyelid. In this manner, the sensor 25 is advantageously capable of detecting when the driver eyelid 12 closes and opens by generating and transmitting first and second eyelid detection signals to the microchip 31 when the driver eyelid 12 closes and opens respectively. A transducer 32 may be attached to the ear piece 20 and adapted to be placed in the driver ear 11. A communication interface 36 may be used to enable the microchip 31 to effectively communicate with the transducer 32.

In this way, the microchip 31 preferably determines a number of continuous occurrences of the first and second eyelid detection signals per a unit of time and thereby generates and transmits true and false control signals to the transducer 32 when the number of continuous occurrences of the first and second eyelid detection signals is above and below a threshold number of continuous occurrences within the unit of time respectively. As a non-limiting example, the unit of time may be 2 seconds. When sensor 25 detects the eyelid at a closed position, the a first eyelid detection signal is sent to microchip 31. As long as the eyelid remains closed, continuous first eyelid detection signals may be sent every half-second, for example. Thus, if 4 or more continuous first eyelid detection signals are sent within the 2 second unit of time, the microchip 31 toggles the transducer 32 to an on mode for audibly alerting (waking up) the driver. Such an arrangement of components provides the unexpected and unpredicted advantage of providing a discrete device 10 on the driver's ear 11 so that the sensor 25 may be in close proximity to the eyelid and thereby detect opening and closing of the driver's eyelid. Such a discrete arrangement of components ensures the driver is quickly and accurately notified when he/she begins to nod off at the wheel.

Figure 8:
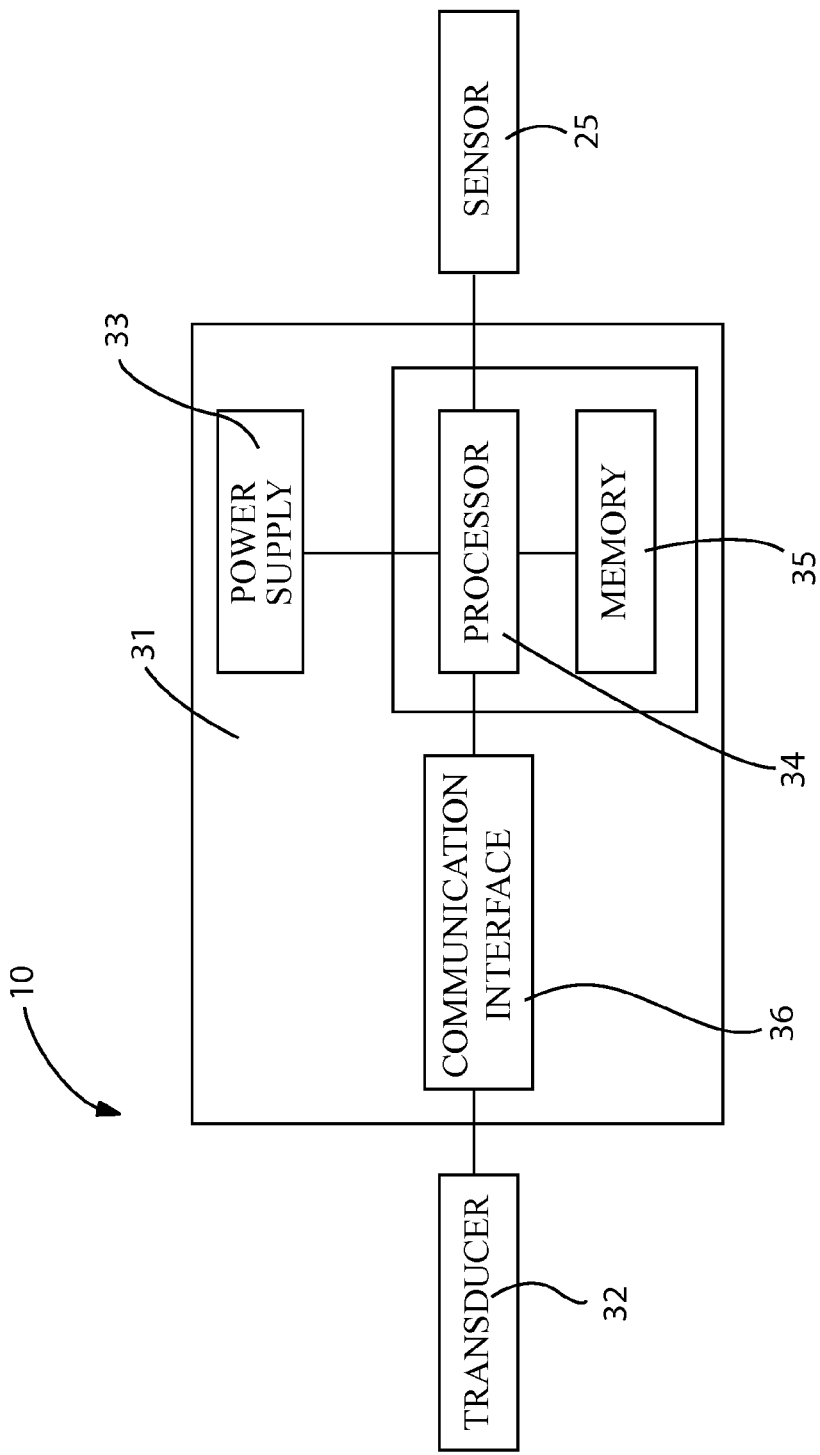
FIG. 8 is a high level schematic block diagram showing the interrelationship between the major electronic components.

As best shown in FIG. 8, the microchip 31 may include a processor 34 and a memory 35 communicatively coupled to the processor 34. The memory 35 may include software instructions, when executed by the processor 34, which may cause the transducer 32 to selectively emit an alert signal such as a loud pitching noise, for example. Such software instructions may include a control logic algorithm that may include the chronological steps of: a. upon receiving an initial signal of the first and second eyelid detection signals, determining whether the initial signal is the first eyelid detection signal; b. if yes, initiating a time count; c. if no, repeating step a.; d. upon receiving a subsequent signal of the first and second eyelid detection signals, determining whether the initial signal is unique to the subsequent signal; e. if the initial signal is unique to the subsequent signal, ending the time count and repeating step a.; f. if the initial signal is the same as the subsequent signal, ending the time count and counting the number of continuous occurrences of the first eyelid detection signals. Such a control logic algorithm provides the unpredicted and unexpected benefit of initially determining whether the eyelid is closed and thereafter determining whether the eyelid remains closed (such as nodding off at the wheel) or quickly opens within the unit of time (such as a blinking movement of the eyelid).

Such a control logic algorithm may further include the chronological steps of: g. if the number of continuous occurrences of the first eyelid detection signal is above the threshold number of continuous occurrences within the unit of time, generating and transmitting the true control signal to the transducer 32; and h. if the number of continuous occurrences of the first eyelid detection signal is below the threshold number of continuous occurrences within the unit of time, generating and transmitting the false control signal to the transducer 32. Such a control logic algorithm provides the unexpected and unpredictable advantage of detecting the driver's eye when it is closed for an dangerous length of time (beyond 2 seconds, for example) and to activate the transducer 32 to emit an audio alarm into the driver's ear 11 before the driver falls asleep at the wheel.

Referring now to FIGS. 1-4, the ear piece 20 may include a hook-shaped member 21 having an arcuate-shaped proximal end portion 22 and a linear distal end portion 23. As perhaps best shown in FIG. 1, the arcuate-shaped proximal end portion 22 may be adapted to be positioned about the driver ear 11. The linear distal end portion 23 may be adapted to terminate at a corner of the driver eyelid 12. A flange member 24 may be outwardly extended from the hook-shaped member 21 and adapted to be inserted into the driver ear 11. The transducer 32 may further be attached to a tip of the flange member 24. Such an arrangement provides the unexpected and unpredictable advantage of ergonomically positioning the ear piece 20 about the user ear in such a manner that the user can comfortably wear the device 10 and ensure the sensor 25 lays proximate to the corner of the eyelid.

Referring to FIGS. 4-6, the linear distal end portion 23 may further be linearly reciprocated along an axial path 90 while the proximal end portion 22 remains positioned about the driver ear 11. As a non-limiting example, a plurality of apertures 26 may be located at suitable locations on the distal end portion 23 such that a detent 27 may be used to selectively lock the distal end portion 23 at extended and retracted positions defined along the axial path 90. FIGS. 4-6 show the location of the detent 27 in exemplary first, second and third positions respectively. Such an arrangement provides the unexpected and unpredictable advantage of adjusting the sensor 25 position to a desired position located proximate to the driver eyelid 12 thereby ensuring eyelid movement is accurately and continuously detected during extended driving periods.

The present disclosure may further include a method of utilizing an electronic alerting device 10 adapted to be worn on an ear 11 of a driver for ensuring that the driver remains alert while operating a vehicle. Such a method may include the chronological steps of: providing an ear piece 20 including a microchip 31 housed therein; providing and locating a sensor 25 at an outer surface of the ear piece 20; providing and attaching a transducer 32 to the ear piece 20; providing a communication interface 36 for enabling the microchip 31 to communicate with the transducer 32; wearing the ear piece 20 at the driver ear 11; and placing the transducer 32 in the driver ear 11.

Such a method may further include the chronological steps of: upon detecting when a driver eyelid 12 closes and opens, the sensor 25 generating and transmitting first and second eyelid 12 detection signals to the microchip 31 respectively; the microchip 31 determining a number of continuous occurrences of the first and second eyelid 12 detection signals per a unit of time; and the microchip 31 generating and transmitting true and false control signals to the transducer 32 when the number of continuous occurrences of the first and second eyelid detection signals is above and below a threshold number of continuous occurrences within the unit of time respectively.

According to various embodiments of the present disclosure, the device 10 may be worn along the driver face and secured about the driver ear 11 by hooking the arcuate-shaped proximal end portion 22 around a user's ear 11 such that the linear distal end portion 23 preferably extends along a temporal area proximate to the driver's eyelid.

According to various embodiments of the present disclosure, sensor 25 may sense when an eyelid 12 has dipped to a closed position, for example, when a user begins to nod off, and thus sounds conspicuous audible alarm via the transducer 32. Power to the device 10 may be provided by an internal battery source 33.

According to various embodiments of the present disclosure, the processor 34 may include a microprocessor or other devices capable of being programmed or configured to perform computations and instruction processing in accordance with the invention. Such other devices may include microcontrollers, digital signal processors (DSP), Complex Programmable Logic Device (CPLD), Field Programmable Gate Arrays (FPGA), application-specific integrated circuits (ASIC), discrete gate logic, and/or other integrated circuits, hardware or firmware in lieu of or in addition to a microprocessor. Functions and process steps described herein may be performed using programmed computer devices and related hardware, peripherals, equipment and networks. When programmed, the computing devices are configured to perform functions and carry out steps in accordance with principles of the invention. Such programming may comprise operating systems, software applications, software modules, scripts, files, data, digital signal processors (DSP), application-specific integrated circuit (ASIC), discrete gate logic, or other hardware, firmware, or any conventional programmable software, collectively referred to herein as a module.

According to various embodiments of the present disclosure, the memory 35 includes programmable software instructions that are executed by the processor 34. In particular, the programmable software instructions include a plurality of chronological operating steps that define a control logic algorithm for performing the intended functions of the present invention. Such software instructions may be written in a variety of computer program languages such as C++, FORTRAN and Pascal, for example. One skilled in the art understands that such software instructions may contain various Boolean logic processes that perform the intended function of the present invention. Therefore, the specific source or object code of the software program is not intended to be a limiting factor in executing the present invention's intended function. The memory 35, which enables storage of data and programs, may include RAM, ROM, flash memory and any other form of readable and writable storage medium known in the art or hereafter developed.

According to various embodiments of the present disclosure, one of more sensor(s) 25, such as a motion sensor may be provided to cause the present invention for detecting an event, for example. Active and/or passive sensors may be used to react to detectable subject matter such as light or changes in noise. However, the invention is not limited to a particular type of sensor. Those skilled in the art will appreciate that other sensors may be used without departing from the scope of the invention. Examples of such other sensors include pressure sensitive pads; optical sensors configured to sense light reflected from the eye; or any other sensor capable of providing motion detection capability in accordance with principles of the invention.

There are several significant benefits and advantages associated with the electronic alerting device 10. As an example, the device 10 would offer a simple and convenient means of ensuring that weary drivers remain alert while behind the wheel for extend periods of time. A compact, non-cumbersome electronic device that can be comfortably worn on the ear 11 and about the face, the device 10 would effectively help motorists maintain awareness, whether they are driving during the day or at night. As a result, the device 10 will alleviate the risk of accidents on the roads, saving the lives of the drivers and fellow motorists. While it should be noted that one who is extremely exhausted should not attempt to drive, the device 10 would prove effective when driver sleepiness suddenly occurs while on the road. As such, students who spend too many waking hours studying, individuals who work night shifts and especially long distance truck drivers would certainly appreciate the benefits afforded by the device 10.

According to various embodiments of the present disclosure, the driver may adjust a volume of the transducer 32 to a desired level by adjusting the volume control 32a in a conventional manner.

According to various embodiments of the present disclosure, the electronic alerting device 10 may feature a Bluetooth interface.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention. In particular, with respect to the above description, it is to be realized that the optimum dimensional relationships for the parts of the present invention may include variations in size, materials, shape, form, function and manner of operation.

What is claimed as new and what is desired to secure by Letters Patent of the United States is:

1. An electronic alerting device adapted to be worn on an ear of a driver for ensuring that the driver remains alert while operating a vehicle, said electronic alerting device comprising:
   an earpiece adapted to be worn at the driver ear, said earpiece including a microchip housed therein;
   a sensor located at an outer surface of said earpiece and being capable of detecting when a driver eyelid closes and opens, said sensor generating and transmitting first and second eyelid detection signals to said microchip when the driver eyelid closes and opens respectively;
   a transducer attached to said earpiece and adapted to be placed in the driver ear;
   wherein said earpiece comprises a hook-shaped member comprising
      an arcuate-shaped proximal end portion adapted to be positioned about the driver ear;
      a linear distal end portion adapted to terminate at a corner of the driver eyelid;
      wherein said sensor is located on said linear distal end portion substantially orthogonal to said arcuate-shaped proximal end portion and configured to remain on said linear distal end portion on a side of the driver's face;
a flange member outwardly extended from said hook-shaped member and adapted to be inserted into the driver ear;
wherein said transducer is attached to a tip of said flange member;
a communication interface enabling said microchip to communicate with said transducer;
wherein said microchip determines a number of continuous occurrences of said first and second eyelid detection signals per a unit of time, said microchip generating and transmitting true and false control signals to said transducer when said number of continuous occurrences of said first and second eyelid detection signals is above and below a threshold number of continuous occurrences within the unit of time respectively;
wherein said microchip comprises:
 a processor; and
 a memory communicatively coupled to said processor, said memory including software instructions, when executed by said processor, said processor causing said transducer to selectively emit an alert signal; and,
wherein said software instructions comprise: a control logic algorithm including the chronological steps of
 upon receiving an initial signal of said first and second eyelid detection signals, determining whether said initial signal is said first eyelid detection signal;
 if yes, initiating a time count;
 if no, repeating said determining whether said initial signal is said first eyelid detection signal upon receiving an initial signal of said first and second eyelid detection signals;
 upon receiving a subsequent signal of said first and second eyelid detection signals, determining whether said initial signal is unique to said subsequent signal;
 if said initial signal is unique to said subsequent signal, ending said time count and repeating said determining whether said initial signal is said first eyelid detection signal upon receiving an initial signal of said first and second eyelid detection signals;
 if said initial signal is the same as said subsequent signal, ending said time count and counting said number of continuous occurrences of said first eyelid detection signals;
 if said number of continuous occurrences of said first eyelid detection signal is above said threshold number of continuous occurrences within said unit of time, generating and transmitting said true control signal to said transducer; and
 if said number of continuous occurrences of said first eyelid detection signal is below said threshold number of continuous occurrences within said unit of time, generating and transmitting said false control signal to said transducer.

2. The electronic alerting device of claim 1, wherein said linear distal end portion is linearly reciprocated along an axial path while said proximal end portion remains positioned about the driver ear.

3. An electronic alerting device adapted to be worn on an ear of a driver for ensuring that the driver remains alert while operating a vehicle, said electronic alerting device comprising:
an earpiece adapted to be worn at the driver ear, said earpiece including a microchip housed therein;
a sensor located at an outer surface of said earpiece and being capable of detecting when a driver eyelid closes and opens, said sensor generating and transmitting first and second eyelid detection signals to said microchip when the driver eyelid closes and opens respectively;
a transducer attached to said earpiece and adapted to be placed in the driver ear;
wherein said earpiece comprises a hook-shaped member comprising
 an arcuate-shaped proximal end portion adapted to be positioned about the driver ear;
 a linear distal end portion adapted to terminate at a corner of the driver eyelid;
 wherein said sensor is located on said linear distal end portion substantially orthogonal to said arcuate-shaped proximal end portion and configured to remain on said linear distal end portion on a side of the driver's face;
a flange member outwardly extended from said hook-shaped member and adapted to be inserted into the driver ear;
wherein said transducer is attached to a tip of said flange member;
a communication interface enabling said microchip to communicate with said transducer;
wherein said microchip determines a number of continuous occurrences of said first and second eyelid detection signals per a unit of time, said microchip generating and transmitting true and false control signals to said transducer when said number of continuous occurrences of said first and second eyelid detection signals is above and below a threshold number of continuous occurrences within the unit of time respectively;
wherein said microchip comprises:
 a processor; and
 a memory communicatively coupled to said processor, said memory including software instructions, when executed by said processor, said processor causing said transducer to selectively emit an alert signal;
wherein said software instructions comprise: a control logic algorithm including the chronological steps of
 upon receiving an initial signal of said first and second eyelid detection signals, determining whether said initial signal is said first eyelid detection signal;
 if yes, initiating a time count;
 if no, repeating said determining whether said initial signal is said first eyelid detection signal upon receiving an initial signal of said first and second eyelid detection signals;
 upon receiving a subsequent signal of said first and second eyelid detection signals, determining whether said initial signal is unique to said subsequent signal;
 if said initial signal is unique to said subsequent signal, ending said time count and repeating said determining whether said initial signal is said first eyelid detection signal upon receiving an initial signal of said first and second eyelid detection signals;
 if said initial signal is the same as said subsequent signal, ending said time count and counting said number of continuous occurrences of said first eyelid detection signals;
 if said number of continuous occurrences of said first eyelid detection signal is above said threshold number of continuous occurrences within said unit of time, generating and transmitting said true control signal to said transducer; and if said number of continuous occurrences of said first eyelid detection signal is below said threshold number of continuous occurrences within said unit of time, generating and transmitting said false control signal to said transducer; and, wherein said sensor is a passive sensor.

4. The electronic alerting device of claim 3, wherein said linear distal end portion is linearly reciprocated along an axial path while said proximal end portion remains positioned about the driver ear.

5. A method of utilizing an electronic alerting device adapted to be worn on an ear of a driver for ensuring that the driver remains alert while operating a vehicle, said method comprising the chronological steps of:

providing an earpiece including a microchip housed therein;

providing and locating a sensor at an outer surface of said earpiece;

wherein said earpiece comprises a hook-shaped member comprising an arcuate-shaped proximal end portion adapted to be positioned about the driver ear;

a linear distal end portion adapted to terminate at a corner of the driver eyelid;

wherein said sensor is located on said linear distal end portion substantially orthogonal to said arcuate-shaped proximal end portion and configured to remain on said linear distal end portion on a side of the driver's face;

a flange member outwardly extended from said hook-shaped member and adapted to be inserted into the driver ear;

providing and attaching a transducer to said earpiece;

wherein said transducer is attached to a tip of said flange member;

providing a communication interface for enabling said microchip to communicate with said transducer;

upon detecting when a driver eyelid closes and opens, said sensor generating and transmitting first and second eyelid detection signals to said microchip respectively;

said microchip determining a number of continuous occurrences of said first and second eyelid detection signals per a unit of time;

said microchip generating and transmitting true and false control signals to said transducer when said number of continuous occurrences of said first and second eyelid detection signals is above and below a threshold number of continuous occurrences within the unit of time respectively;

wherein said microchip comprises:

a processor; and a memory communicatively coupled to said processor, said memory including software instructions, when executed by said processor, said processor causing said transducer to selectively emit an alert signal; and, wherein said software instructions comprise: a control logic algorithm including the chronological steps of upon receiving an initial signal of said first and second eyelid detection signals, determining whether said initial signal is said first eyelid detection signal;

if yes, initiating a time count;

if no, repeating said determining whether said initial signal is said first eyelid detection signal upon receiving an initial signal of said first and second eyelid detection signals;

upon receiving a subsequent signal of said first and second eyelid detection signals, determining whether said initial signal is unique to said subsequent signal;

if said initial signal is unique to said subsequent signal, ending said time count and repeating said determining whether said initial signal is said first eyelid detection signal upon receiving an initial signal of said first and second eyelid detection signals;

if said initial signal is the same as said subsequent signal, ending said time count and counting said number of continuous occurrences of said first eyelid detection signals;

if said number of continuous occurrences of said first eyelid detection signal is above said threshold number of continuous occurrences within said unit of time, generating and transmitting said true control signal to said transducer; and if said number of continuous occurrences of said first eyelid detection signal is below said threshold number of continuous occurrences within said unit of time, generating and transmitting said false control signal to said transducer.

6. The electronic alerting device of claim 1, wherein said sensor is a passive sensor.

7. The method of utilizing an electronic alerting device of claim 5, wherein said providing said sensor comprises providing a passive sensor.

8. The electronic alerting device of claim 1, wherein said sensor is a motion sensor.

9. The method of utilizing an electronic alerting device of claim 5, wherein said providing said sensor comprises providing a motion sensor.

10. An electronic alerting device adapted to be worn on an ear of a driver for ensuring that the driver remains alert while operating a vehicle, said electronic alerting device comprising:

an earpiece adapted to be worn at the driver ear, said earpiece including a microchip housed therein;

a sensor located at an outer surface of said earpiece and being capable of detecting when a driver eyelid closes and opens, said sensor generating and transmitting first and second eyelid detection signals to said microchip when the driver eyelid closes and opens respectively;

a transducer attached to said earpiece and adapted to be placed in the driver ear;

wherein said earpiece comprises a hook-shaped member comprising an arcuate-shaped proximal end portion adapted to be positioned about the driver ear;

a linear distal end portion adapted to terminate at a corner of the driver eyelid;

wherein said sensor is located on said linear distal end portion substantially orthogonal to said arcuate-shaped proximal end portion and configured to remain on said linear distal end portion on a side of the driver's face;

a flange member outwardly extended from said hook-shaped member and adapted to be inserted into the driver ear;

wherein said transducer is attached to a tip of said flange member;

a communication interface enabling said microchip to communicate with said transducer;

wherein said microchip determines a number of continuous occurrences of said first and second eyelid detection signals per a unit of time, said microchip generating and transmitting true and false control signals to said transducer when said number of continuous occurrences of said first and second eyelid detection signals is above and below a threshold number of continuous occurrences within the unit of time respectively;

wherein said microchip comprises:
- a processor; and
- a memory communicatively coupled to said processor, said memory including software instructions, when executed by said processor, said processor causing said transducer to selectively emit an alert signal;

wherein said software instructions comprise: a control logic algorithm including the chronological steps of upon receiving an initial signal of said first and second eyelid detection signals, determining whether said initial signal is said first eyelid detection signal;

if yes, initiating a time count;

if no, repeating said determining whether said initial signal is said first eyelid detection signal upon receiving an initial signal of said first and second eyelid detection signals;

upon receiving a subsequent signal of said first and second eyelid detection signals, determining whether said initial signal is unique to said subsequent signal;

if said initial signal is unique to said subsequent signal, ending said time count and repeating said determining whether said initial signal is said first eyelid detection signal upon receiving an initial signal of said first and second eyelid detection signals;

if said initial signal is the same as said subsequent signal, ending said time count and counting said number of continuous occurrences of said first eyelid detection signals;

if said number of continuous occurrences of said first eyelid detection signal is above said threshold number of continuous occurrences within said unit of time, generating and transmitting said true control signal to said transducer; and if said number of continuous occurrences of said first eyelid detection signal is below said threshold number of continuous occurrences within said unit of time, generating and transmitting said false control signal to said transducer; and, wherein said sensor is a motion sensor.

11. The electronic alerting device of claim 10, wherein said linear distal end portion is linearly reciprocated along an axial path while said proximal end portion remains positioned about the driver ear.

* * * * *